(12) United States Patent
Goldberg et al.

(10) Patent No.: US 8,317,861 B2
(45) Date of Patent: Nov. 27, 2012

(54) ANTIMICROBIAL INDWELLING VOICE PROSTHESIS

(75) Inventors: Jeffrey L. Goldberg, San Diego, CA (US); Edmund V. Seder, Santa Barbara, CA (US); Jesse N. Nelson, Oxnard, CA (US); Juan M. Madrigal, Oxnard, CA (US)

(73) Assignee: Helix Medical, LLC, Plymouth, MI (US)

( * ) Notice: Subject to any disclaimer, the term of this patent is extended or adjusted under 35 U.S.C. 154(b) by 100 days.

(21) Appl. No.: 11/093,351

(22) Filed: Mar. 29, 2005

(65) Prior Publication Data
US 2005/0171602 A1    Aug. 4, 2005

Related U.S. Application Data

(63) Continuation-in-part of application No. 09/833,961, filed on Apr. 11, 2001, now abandoned.

(51) Int. Cl.
*A61F 2/20* (2006.01)
(52) U.S. Cl. .......................................................... 623/9
(58) Field of Classification Search .................. 623/9
See application file for complete search history.

(56) References Cited

U.S. PATENT DOCUMENTS

| | | | |
|---|---|---|---|
| 3,445,420 A | 5/1969 | Kookootsedes et al. | |
| 3,932,627 A | 1/1976 | Margraf | |
| 3,952,335 A | 4/1976 | Sorce et al. | |
| 4,040,428 A | 8/1977 | Clifford | |
| 4,054,139 A | 10/1977 | Crossley | |
| 4,435,853 A | 3/1984 | Blom et al. | |
| 4,483,688 A | 11/1984 | Akiyama | |
| 4,563,485 A | 1/1986 | Fox, Jr. et al. | |
| 4,581,028 A | 4/1986 | Fox, Jr. et al. | |
| 4,592,920 A | 6/1986 | Murtfeldt | |
| 4,603,152 A | 7/1986 | Laurin et al. | |
| 4,610,691 A * | 9/1986 | Depel et al. | 623/9 |
| 4,612,337 A | 9/1986 | Fox, Jr. et al. | |
| 4,614,516 A * | 9/1986 | Blom et al. | 623/9 |
| 4,615,705 A | 10/1986 | Scales et al. | |
| 4,677,143 A | 6/1987 | Laurin et al. | |
| 4,911,716 A | 3/1990 | Blom et al. | |

(Continued)

FOREIGN PATENT DOCUMENTS
DE    19754432    6/1999
(Continued)

OTHER PUBLICATIONS

Everaert et al. "Biofilm Formation in Vivo on PerfluroAlkylsiloxane-Modified Voice Prostheses" Arch Otolaryngol Head Nec Surg. vol. 125. pp. 1329-1332 (1999).

(Continued)

*Primary Examiner* — David Isabella
*Assistant Examiner* — Ann Schillinger
(74) *Attorney, Agent, or Firm* — Harness, Dickey & Pierce, P.L.C.

(57) ABSTRACT

A voice prosthesis comprising a tubular body portion, a valve and a valve seat disposed within the body portion. The valve seat is further comprised of a medical grade elastomer containing a dispersion of an antimicrobial agent. This valve seat extends the life of the prosthesis by retarding the growth of microorganisms. The body portion of the prosthesis may also contain an antimicrobial agent at a concentration that is non-toxic to the tissue it contacts.

8 Claims, 4 Drawing Sheets

U.S. PATENT DOCUMENTS

| | | | |
|---|---|---|---|
| 5,019,096 A | 5/1991 | Fox, Jr. et al. | |
| 5,064,433 A | 11/1991 | Blom et al. | |
| 5,238,749 A | 8/1993 | Cueman et al. | |
| 5,314,470 A | 5/1994 | Persson | |
| 5,391,205 A | 2/1995 | Knight | |
| 5,474,797 A | 12/1995 | Sioshansi et al. | |
| 5,480,432 A | 1/1996 | Suding et al. | |
| 5,507,809 A | 4/1996 | Blom | |
| 5,520,664 A | 5/1996 | Bricault, Jr. et al. | |
| 5,567,495 A | 10/1996 | Modak et al. | |
| 5,578,083 A * | 11/1996 | Laguette et al. | 623/9 |
| 5,624,704 A | 4/1997 | Darouiche et al. | |
| 5,632,775 A | 5/1997 | Suding et al. | |
| 5,693,097 A * | 12/1997 | Laguette et al. | 623/9 |
| 5,772,640 A | 6/1998 | Modak et al. | |
| 5,902,283 A | 5/1999 | Darouiche et al. | |
| 5,928,569 A | 7/1999 | Reo | |
| 5,957,978 A | 9/1999 | Blom | |
| 6,013,711 A | 1/2000 | Lewis et al. | |
| 6,017,587 A | 1/2000 | Kleyer et al. | |
| 6,083,208 A | 7/2000 | Modak et al. | |
| 6,106,505 A | 8/2000 | Modak et al. | |
| 6,358,222 B1 | 3/2002 | Grundei | |
| 6,361,526 B1 * | 3/2002 | Reisdorf et al. | 604/265 |
| 6,558,686 B1 * | 5/2003 | Darouiche | 424/423 |
| 6,596,401 B1 | 7/2003 | Terry et al. | |
| 6,689,302 B2 | 2/2004 | Reisdorf et al. | |
| 6,716,895 B1 | 4/2004 | Terry | |
| 6,887,270 B2 | 5/2005 | Miller et al. | |
| 6,948,526 B2 | 9/2005 | Seder et al. | |
| 7,081,133 B2 | 7/2006 | Chinn et al. | |
| 7,166,128 B1 * | 1/2007 | Persson | 623/9 |
| 7,393,547 B2 | 7/2008 | Nelson | |
| 7,520,897 B2 | 4/2009 | Seder et al. | |
| 2002/0022136 A1 | 2/2002 | Valade et al. | |
| 2002/0193879 A1 * | 12/2002 | Seder et al. | 623/9 |
| 2004/0116551 A1 | 6/2004 | Terry | |
| 2004/0187941 A1 | 9/2004 | Seder et al. | |
| 2004/0214939 A1 | 10/2004 | Patel et al. | |
| 2005/0020844 A1 | 1/2005 | Nelson | |
| 2005/0049350 A1 | 3/2005 | Tonapi et al. | |
| 2005/0148721 A1 | 7/2005 | Tonapi et al. | |
| 2005/0161859 A1 | 7/2005 | Miller et al. | |
| 2005/0239940 A1 | 10/2005 | Shima et al. | |
| 2005/0256573 A1 | 11/2005 | Seder et al. | |
| 2006/0045899 A1 | 3/2006 | Sarangapani | |
| 2006/0047043 A1 | 3/2006 | Nakayoshi et al. | |
| 2009/0026660 A1 | 1/2009 | Nelson et al. | |

FOREIGN PATENT DOCUMENTS

| | | |
|---|---|---|
| EP | 0222 509 A2 * | 10/1986 |
| EP | 0222509 | 5/1987 |
| WO | WO 97/14447 | 4/1997 |
| WO | WO 97/45075 * | 12/1997 |
| WO | WO 98/04463 | 2/1998 |
| WO | WO 98/08463 * | 3/1998 |
| WO | WO 01/43788 | 6/2001 |
| WO | WO 01/43788 A2 | 6/2001 |
| WO | WO 02/077095 | 10/2002 |
| WO | WO 02/083031 | 10/2002 |
| WO | WO 03/057083 | 7/2003 |
| WO | WO 03/082983 | 10/2003 |
| WO | WO 2004/017738 | 3/2004 |
| WO | WO 2004/046233 | 6/2004 |
| WO | WO 2004/050753 | 6/2004 |
| WO | WO 2005/014074 | 2/2005 |
| WO | WO 2005/087135 | 9/2005 |
| WO | WO 2006/023232 | 3/2006 |

OTHER PUBLICATIONS

Saidi et al. "In Vivo Resistance to Bacterial Biofilm Formation on Tympanostomy Tubes as a Function of Tube Material" Otolaryngology—Head and Neck Surgery. vol. 120, No. 5, pp. 621-627 (1999)—Abstract Only.

Busscher H., et al., Chapter 12, "Biofilm Formation and its Prevention on Silicone Rubber Voice Prostheses," In: Blom ED, Singer MI, Harnaker R (eds) Tracheoesophageal Voice Restoration Following Total Laryngectomy, Singular Publishing Group, San Diego. 1998: 89-102.

Kress, P. et al., "Klinische Anwendung einer Stimmprothese mit silberoxidhaltigem Ventil (Blom-Singer® Advantage)—Biofilmresistenz, Prothesen-verweildauer und Indikation," Laryngo-Rhino-Otol, vol. 85, pp. 1-5 (Mar. 16, 2006). German language document with English abstract.

Leder, S. et al., "Voice Restoration With the Advantage Tracheoesophageal Voice Prosthesis," Otolaryngology—Head and Neck Surgery, vol. 133, No. 5, pp. 681-684 (Nov. 2005).

* cited by examiner

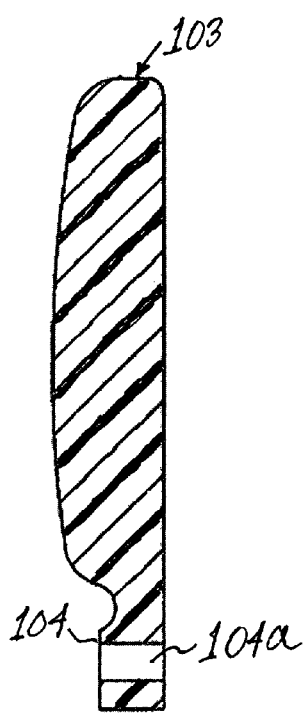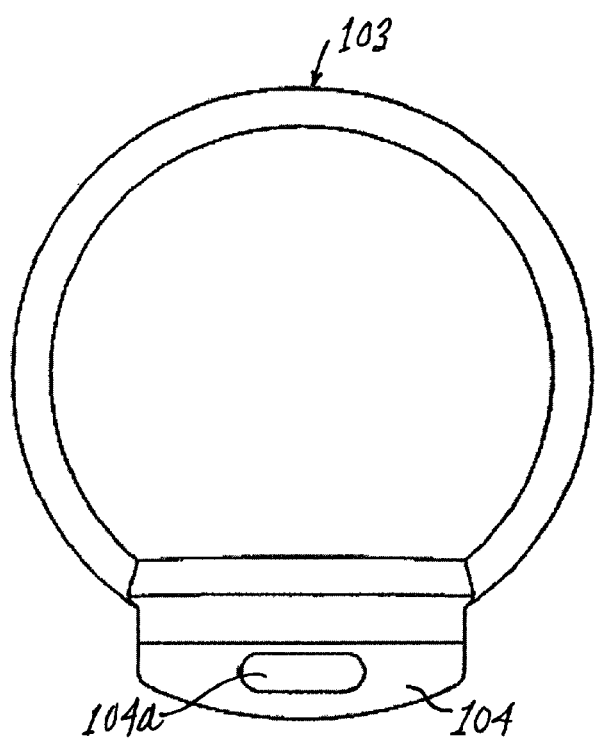
Figure 3
Figure 4

ANTIMICROBIAL INDWELLING VOICE PROSTHESIS

This application is a continuation-in-part of pending U.S. patent application Ser. No. 09/833,961, filed Apr. 11, 2001 now abandoned.

BACKGROUND OF THE INVENTION

1. Field of the Invention

The present invention relates to microbial-resistant medical devices and, more particularly, to a voice prosthesis having a valve seat which retards growth of microorganisms.

2. Prior Art

There are several options for restoring speech to patients who have had their larynx removed. One procedure is to surgically create a puncture or fistula between the trachea and the esophagus. A tracheoesophageal voice prosthesis containing a one-way valve such as a BLOM-SINGER® voice prosthesis is inserted into the tracheoesophageal fistula. The one-way valve protects the airway during swallowing but opens under positive pressure from the trachea. The voice prosthesis, thus, permits a patient to divert air from the lungs into the esophagus and out through the mouth. Speech is created during passage of air through the upper part of the esophagus.

The voice prosthesis maintains the patency of the fistula, transfers air from the trachea to the esophagus for voice production and prevents esophageal leakage into the trachea during swallowing. The oral cavity which extends into the throat can have a high microbial population. The prosthesis, being in contact with moisture in a warm, dark, nutrient rich environment, is subject to growth of commonly found microorganisms, typically Candida, on the valve, valve seat and the retaining flange. The microbial growth on and into the soft silicone resin can interfere with function of the valve and can cause the valve seat to warp and the valve to leak.

A voice prosthesis has been developed that can remain in place in the tracheoesophageal fistula for months, depending on the patient and conditions of use. The patient can confidently use the prosthesis for longer periods than the non-indwelling voice prosthesis. The longer dwelling voice prosthesis is not removable by the patient. Trips to a health care specialist to remove and replace the prosthesis are greatly extended providing increased comfort and lower cost to the patient.

Blom, in U.S. Pat. No. 4,435,853 describes a soft voice prosthesis for use over an extended period of time. This voice prosthesis does not include the use of an antimicrobial agent.

Persson, in U.S. Pat. No. 5,314,470 discloses a soft voice prosthesis that includes a rigid stiffening ring 14 inserted into a groove in the soft body of the prosthesis.

U.S. Pat. No. 5,578,083 issued Nov. 26, 1996, discloses the use of a stiff cartridge to support the soft silicone prosthesis and to provide a seat for the valve. However, microbial growth still proceeds to a point at which the valve can not be reliably sealed.

Although the rigid valve seat designs reduce microbial ingrowth into the valve seat material, they do not retard microbial growth. Leaking can be due to distortion of the valve body adjacent to the seat of the valve and to microbial growth on the seat.

Relevant prior art includes U.S. Pat. Nos. 3,932,627, 4,054,139, 4,483,688, 4,563,485, 4,581,028, 4,603,152, 4,612,337, 4,615,705, 5,019,096, 5,567,495, 5,624,704, 5,772,640, 5,902,283, 6,083,208 and 6,106,505.

SUMMARY

In accordance with the present invention, antimicrobial agents are compounded into either, or both, the valve and valve seat of a voice prosthesis. The antimicrobial parts remain free of microbial growth in situ for an extended period which contributes to longer use of the prosthesis in vivo.

The body of the voice prosthesis is formed of an elastomer and the valve seat is made with an antimicrobial agent incorporated therein. The body of the prosthesis may have some antimicrobial properties as long as the tissue-contacting surface of the body is not toxic to tissue.

The antimicrobial agent is preferably incorporated in the elastomer by mechanical dispersion into the uncured elastomer. The term "antmicrobial agent", as used herein, means a chemical substance which retards the growth of microorganisms. For example, silicone elastomer can contain an antimicrobial agent such as silver or silver compounds such as silver oxide. Other suitable antimicrobial compounds that may be toxic to tissue such as gold, platinum, copper, zinc metal powder or oxides and salts thereof, can be used in the non-tissue contact regions of the prosthesis. Other antimicrobial agents include organic antimicrobial agents that can be dispersed throughout the raw material such as butyl paraben butyl p-hydroxy benzoate or an alkene carboxylic acid salts such as alkali metal sorbate salt or a halohydroxy aromatic ether such as triclosan (2,4,4'-trichloro-7'hydroxydiphenyl ether.

The features of the invention believed to be novel are set forth with particularity in the appended claims. However the invention itself, both as to organization and method of operation, together with further objects and advantages thereof may be best understood by reference to the following description taken in conjunction with the accompanying drawings.

BRIEF DESCRIPTION OF THE DRAWINGS

FIG. 3 is a cross-sectional view of the valve flap employed in the particularly preferred embodiment shown in FIG. 2.

FIG. 4 is a top view of the flap valve of FIG. 3.

DESCRIPTION OF THE PREFERRED EMBODIMENTS

Providing a voice prosthesis having a microbial-resistant valve seat according to the invention is desirable for extending the time that the prosthesis remains functional in its intended use. Since the growth of a biofilm layer will be retarded, warping of the valve seat is reduced. The microbial resistant surface can be provided by dispersing a microbial agent such as metal, metal oxide or salt or organic antimicrobial agent into the biocompatible elastomer.

Figure 1:
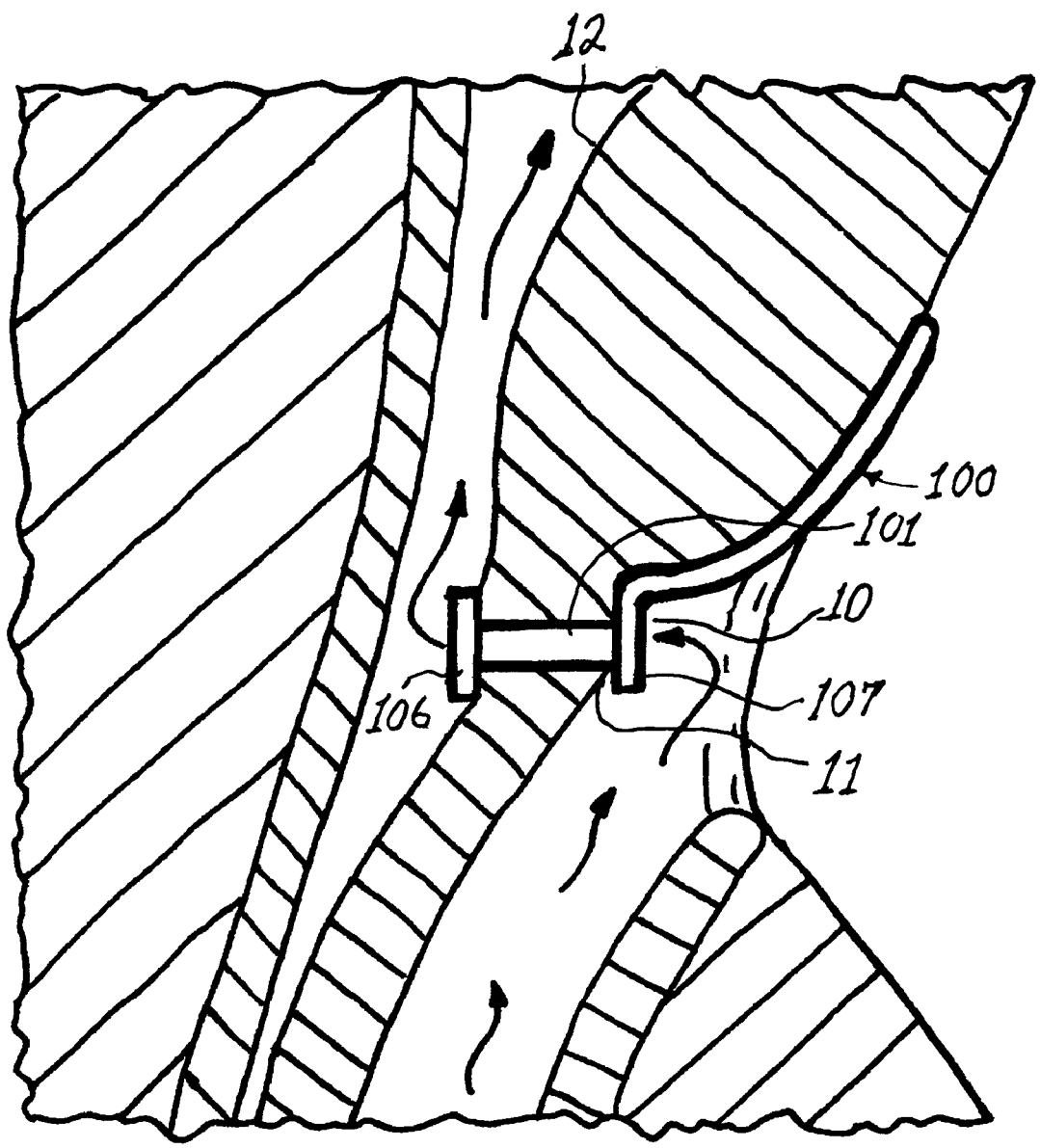
FIG. 1 is a schematic view of a voice prosthesis installed in a tracheoesophageal fistula.

The present invention provides an antimicrobial voice prosthesis and a method for producing the antimicrobial voice prosthesis, which can be applied to any size voice prosthesis. Referring now to FIG. 1, a voice prosthesis 100 is shown inserted into a fistula 10 with the front flange 107 engaging the outer wall 11 of the trachea, and the rear flange 106 engaging the wall 12 of the esophagus. The body portion 101 of the prosthesis 100 prevents the fistula 10 from closing.

Figure 2:
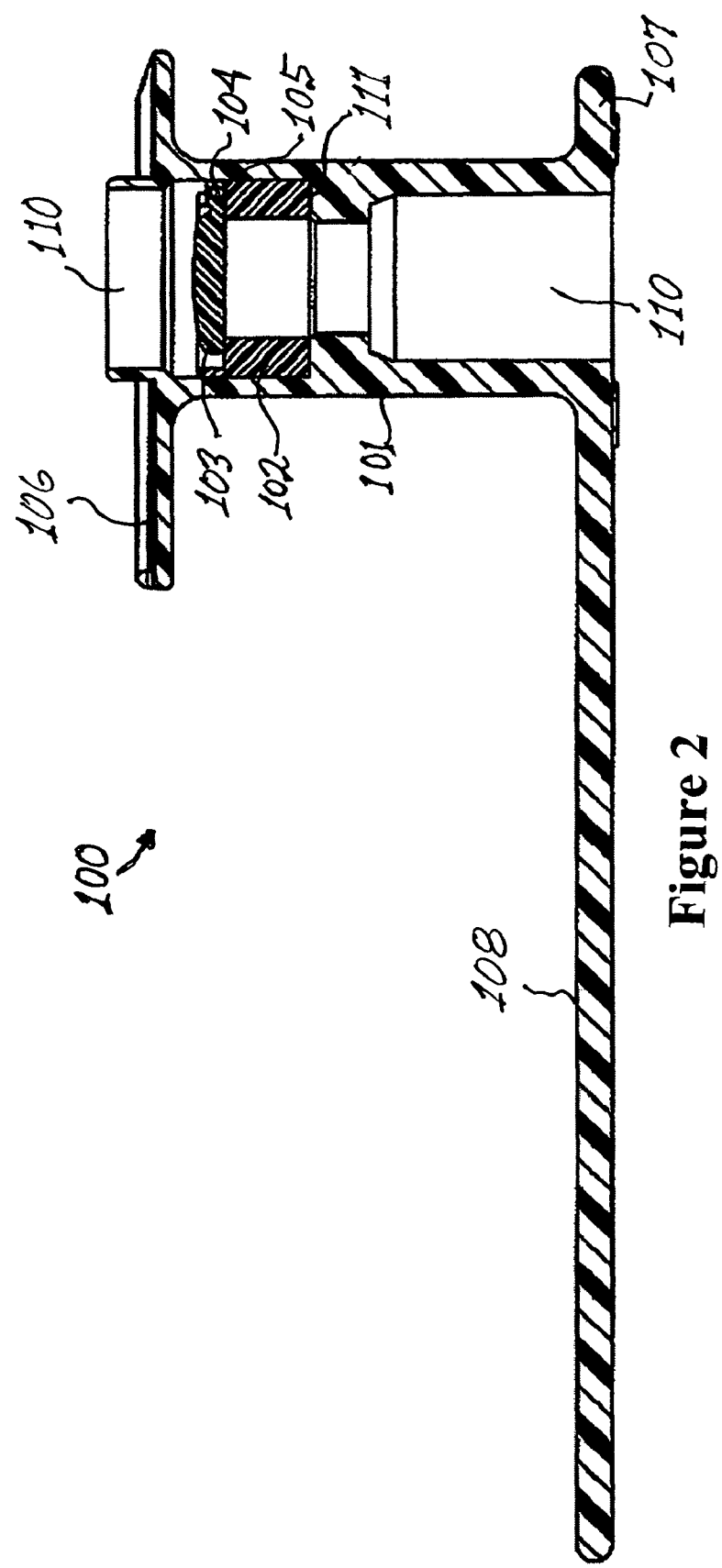
FIG. 2 is a longitudinal cross-sectional view of a preferred embodiment of a voice prosthesis of the present invention.

With reference to FIGS. 2-5, the voice prosthesis of the present invention, indicated at numeral 100 in FIGS. 1 and 2, is similar in operation to the above-described prior art voice prostheses, but lacks a (rigid) cartridge and obviates the need for a stiffening ring around the cartridge as taught in the prior art. The voice prosthesis 100 includes a body portion 101, a valve seat 102 and a flap valve 103. A hinge portion 104 of the valve 103, located on the periphery of the flap valve 103, is located via locating posts 105 (FIGS. 5a and 5b) projecting upwardly from the valve seat 102 and affixed to the valve seat, body wall, or both. The rear flange 106 is unitary with the body portion 101, foldable and dimensioned to fit through the fistula 10 (FIG. 1) and engage the inner wall 12 (FIG. 1) of the esophagus when the device 100 is implanted. The front flange 107 is also unitary with the body portion 101 and has a strap 108 projecting outwardly therefrom that is employed to insert and stabilize the position of the device 100 within the fistula. The strap 108 may further have a section thereon for detachable joinder with an insertion tool.

The prior art devices have not recognized the problems caused by microbial growth on the valve seat and have not provided means for retarding microbial growth on the valve seat. In accordance with an embodiment of the present invention, the valve seat 102 and valve 103 are constructed at least in part from an elastomer, preferably medical grade silicone, having silver oxide dispersed in the elastomer. The lumen 110 in the body portion 101 has a step therein to provide a shoulder 111 in the lumen 110 operable for supporting the valve seat 102. The antimicrobial valve seat 102 can be glued or insertion molded into the lumen 110 of the voice prosthesis body portion 101, and the hinge portion 104 of the (preferably antimicrobial) flap valve 103 glued thereto. Alternatively, the valve seat 102 may be friction fit or physically locked by ledges, grooves, or abutments into the body portion 101 of the voice prosthesis 100 to achieve the same effect.

The important features of the present voice prosthesis are: (a) the valve seat 102 has an antimicrobial agent incorporated within the elastomer and is recessed within the lumen 110 of the body portion; (b) the valve seat 102 is nonreleasably attached to the body portion 101; and (c) the construction obviates the use of a stiffening ring disposed around the valve seat. The placement of the valve seat within the lumen of body portion of the voice prosthesis keeps the antimicrobial material away from tissue contact. The antimicrobial agent is preferably silver oxide ($Ag_2O$) but could comprise other antimicrobial substances compounded into the silicone material.

The preferred manner of providing a surface resistant to microbial growth is to disperse an antimicrobial agent in the elastomer forming the portion of the device not in direct contact with body tissue. The agent can be inorganic such as a salt or oxide of silver, gold, platinum, zinc or copper, preferably silver oxide or organic materials soluble or dispersible in the resin forming the valve or the cartridge such as hydroxy aromatic carboxylic acids, esters thereof or halogenated phenols. The agent is present in the elastomer in an amount effective to deter microbial growth and at a concentration that can be toxic to tissue. The portions of the device in contact with tissue can contain a much lower concentration of the microbial agent at a level non-toxic and non-irritating to tissue.

For example, in the case of silver oxide as taught in the prior art (U.S. Ser. No. 09/833,961, filed Apr. 11, 2001 by two of the present inventors), the concentration of silver oxide in a silicone elastomer effective to deter growth of microbial biofilm is attainable. The body of the device which is in direct contact with tissue can be compounded to include silver oxide.

Figure 5A:
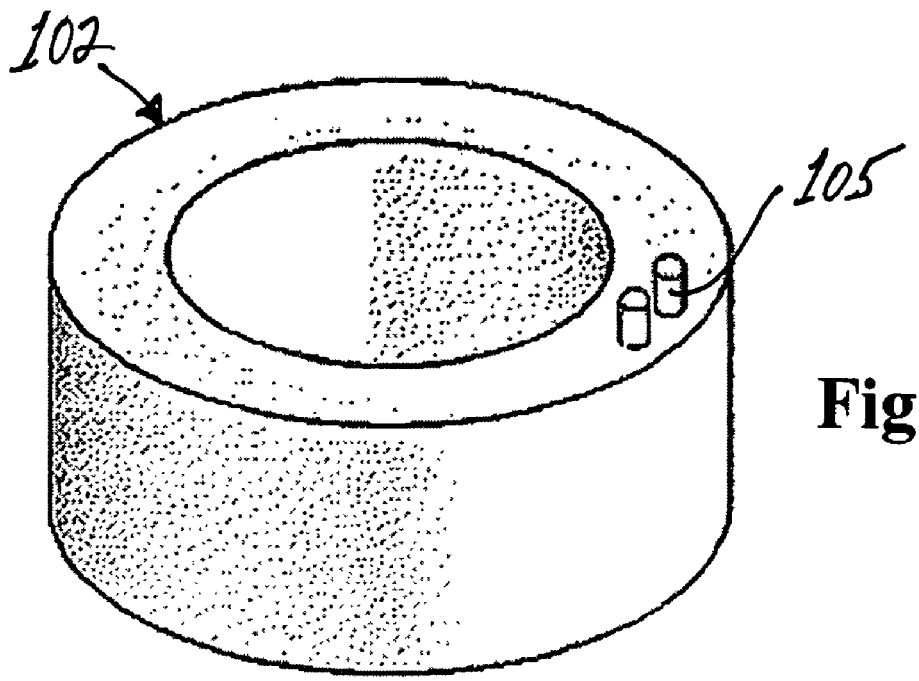
FIG. 5a is a perspective view of a first embodiment of the valve seat used in the particularly preferred embodiment of FIG. 2.
Figure 5B:
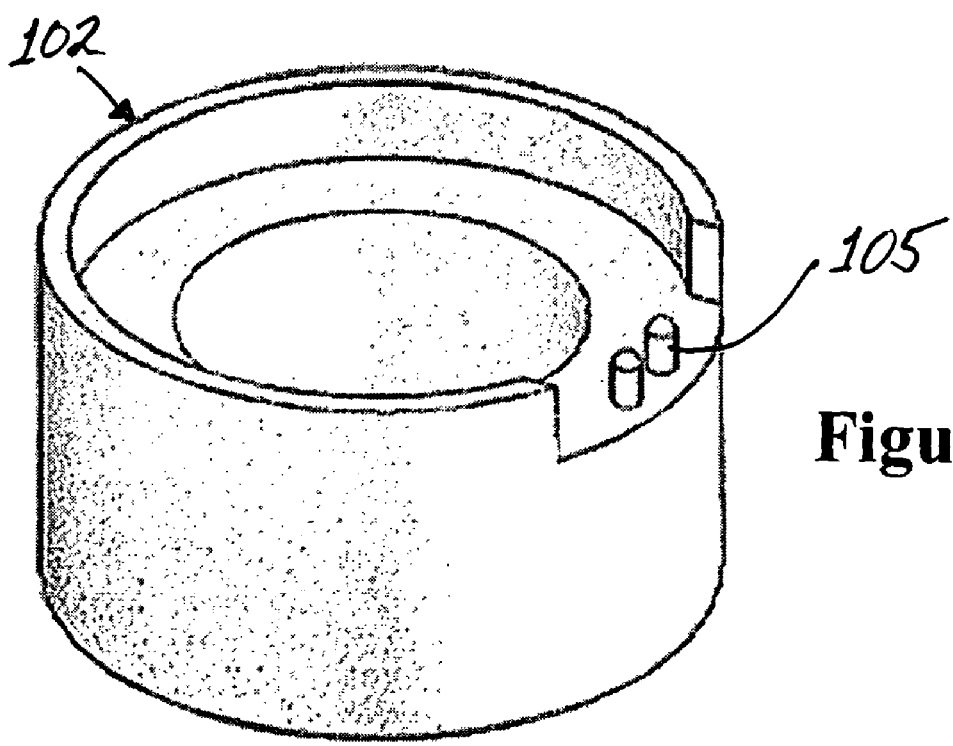
FIG. 5b is a perspective view of a second embodiment of the valve seat used in the particularly preferred embodiment of FIG. 2.

The construction of a voice prosthesis in accordance with the particularly preferred embodiment of the device 100 proceeds as follows. A valve seat 102 comprising a silicone elastomer having silver oxide dispersed therein is molded as shown in FIG. 5a or 5b, then placed on a core pin. The silicone body portion 101 is then insertion molded around the valve seat, and the flap valve 103 is glued, located by the posts 105, on the valve seat 102. The rear flange 106 on the body portion is foldable as shown in the discussion of the prior art devices. The rear flange 106 can be circular or oval.

The particularly preferred embodiment 100 of the voice, prosthesis of the present invention, unlike the cartridge design currently in use, can be made in any size. The valve, valve seat and body portion can be made by liquid injection molding (LIM), transfer molding, or compression molding processes. The voice prosthesis 100, formed with a microbial resistant valve seat (and preferably a antimicrobial valve), will be able to be used for longer periods without the need to remove the prosthesis for cleaning. The body portion of the voice prosthesis can also be compounded with antimicrobial agents at a level acceptable to the FDA.

The voice prosthesis 100 of the present invention is designed for patients who are unable (or resistant) to changing the voice prosthesis as recommended for the non-indwelling, patient-removable low pressure prior art voice prostheses. The indwelling low pressure voice prosthesis 100 has been specifically designed to maintain the placement of the prosthesis in the tracheoesophageal fistula for extended periods of time so that routine changing of the device is not necessary.

While particular embodiments of the present invention have been illustrated and described, it would be obvious to those skilled in the art that various other changes and modifications can be made without departing from the spirit and scope of the invention. For example, antimicrobial agents other than $Ag_2O$ (such as triclosan, buytl paraben, etc.) can be incorporated into the elastomer comprising the valve and valve seat. Materials other than silicone can be employed to fabricate the valve seat seat, such as Kynar PDVF or a polyolefin like polypropylene. The valve and valve seat may be molded as a single, unitary body and insert molded into any French size voice prosthesis. It is therefore intended to cover in the appended claims all such changes and modifications that are within the scope of this invention.

What we claim is:

1. A voice prosthesis device that conducts air between a trachea and an esophagus of a patient, the voice prosthesis device comprising:
    (a) a non-rigid tubular-shaped body portion formed from a first biocompatible elastomer material and defining a forward end comprising a front flange and a rear end comprising a rear flange, wherein said body portion has a first central lumen extending from said forward end to said rear end;
    (b) a molded microbial-resistant valve seat component formed from a second biocompatible elastomer material comprising silver oxide at a concentration sufficient to retard microbial growth on a surface of said valve seat component, wherein said silver oxide is compounded with and substantially dispersed throughout said second biocompatible elastomer material, wherein said molded valve seat component is distinct from said body portion and non-releasably disposed within said central lumen of said body portion, wherein said valve seat component defines a second central lumen;
(c) a valve mounted on said valve seat component; wherein said valve is operable to intermittently seal said second central lumen when said valve contacts a portion of said surface of said valve seat component and operable to open said second central lumen to permit gas to flow therethrough; and
(d) wherein the voice prosthesis device lacks any rigid cartridge or stiffening ring.

2. A voice prosthesis according to claim 1 wherein said first and said second biocompatible elastomers comprise silicone.

3. A voice prosthesis according to claim 1, further comprising silver oxide dispersed in said first biocompatible elastomer in a concentration sufficient to retard microbial growth on said first biocompatible elastomer.

4. A voice prosthesis according to claim 1, wherein the silver oxide in the valve seat component (b) is present therein at a concentration that is toxic to human tissue if in direct contact therewith.

5. A voice prosthesis device that conducts air between a trachea and an esophagus of a patient, the voice prosthesis device comprising:
(a) a non-rigid tubular-shaped body portion formed from a first biocompatible elastomer material and defining a forward end comprising a front flange and a rear end comprising a rear flange, wherein said body portion has a first central lumen extending from said forward end to said rear end and comprises a step defining a shoulder;
(b) a molded microbial-resistant valve seat component formed from a second biocompatible elastomer material comprising silver oxide at a concentration sufficient to retard microbial growth on a surface of said valve seat component, wherein said silver oxide is compounded with and substantially dispersed throughout said second biocompatible elastomer material, wherein said molded valve seat component is distinct from said body portion and non-releasably disposed within said central lumen and operably supported by said shoulder of said body portion, wherein said valve seat component defines a second central lumen;
(c) a valve mounted on said valve seat component; wherein said valve is operable to intermittently seal said second central lumen when said valve contacts a portion of said surface of said valve seat component and operable to open said second central lumen to permit gas to flow therethrough; and
(d) wherein the voice prosthesis device lacks any rigid cartridge or stiffening ring.

6. A voice prosthesis according to claim 5 wherein said first and said second biocompatible elastomers comprise silicone.

7. A voice prosthesis according to claim 5 further comprising silver oxide dispersed in said first elastomer in a concentration sufficient to retard microbial growth on said first elastomer.

8. A voice prosthesis according to claim 5, wherein the silver oxide in the valve seat component (b) is present therein at a concentration that is toxic to human tissue if in direct contact therewith.

\* \* \* \* \*

UNITED STATES PATENT AND TRADEMARK OFFICE
CERTIFICATE OF CORRECTION

| | | Page 1 of 1 |
|---|---|---|
| PATENT NO. | : 8,317,861 B2 | |
| APPLICATION NO. | : 11/093351 | |
| DATED | : November 27, 2012 | |
| INVENTOR(S) | : Goldberg et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 250 days.

Signed and Sealed this
Twenty-first Day of October, 2014

Michelle K. Lee
*Deputy Director of the United States Patent and Trademark Office*